United States Patent [19]

Dorsch et al.

[11] Patent Number: 5,747,539
[45] Date of Patent: May 5, 1998

[54] FLUORINE-CONTAINING BENZOYLGUANIDINES

[75] Inventors: Dieter Dorsch, Ober-Ramstadt; Manfred Baumgarth, Darmstadt; Rolf Gericke, Seeheim; Klaus-Otto Minck, Ober-Ramstadt; Norbert Beier, Reinheim, all of Germany

[73] Assignee: Merck Patent Gesellschaft Mit Beschrankter Haftung, Darmstadt, Germany

[21] Appl. No.: 647,789

[22] Filed: May 15, 1996

[30] Foreign Application Priority Data

May 16, 1995 [DE] Germany .................. 195 17 848.3

[51] Int. Cl.$^6$ .................. C07C 279/22; A61K 31/165; A61K 31/155
[52] U.S. Cl. .................. 514/618; 514/617; 514/622; 514/619; 514/824; 514/866; 564/162; 564/163; 564/164; 564/166; 564/167; 564/168; 564/170; 564/171; 564/176; 564/177; 564/179
[58] Field of Search .................. 514/618, 619, 514/622, 617, 824, 866; 564/162, 163, 164, 166, 167, 168, 170, 171, 176, 177, 179

[56] References Cited

FOREIGN PATENT DOCUMENTS

| 416499 | 9/1990 | European Pat. Off. . |
| 0416499 | 3/1991 | European Pat. Off. . |
| 0556673 | 8/1993 | European Pat. Off. . |
| 0556674 | 8/1993 | European Pat. Off. . |
| 0 640 588 | 3/1995 | European Pat. Off. . |

*Primary Examiner*—Peter O'Sullivan
*Attorney, Agent, or Firm*—Millen, White, Zelano, & Branigan, P.C.

[57] ABSTRACT

Fluorine-containing benzoylguanidines of the formula I

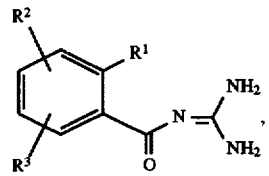

in which $R^1$, $R^2$ and $R^3$ have the meanings indicated, and their physiologically acceptable salts, have antiarrhythmic properties and act as inhibitors of the cellular $Na^+/H^+$ antiporter, for example.

8 Claims, No Drawings

FLUORINE-CONTAINING BENZOYLGUANIDINES

The invention relates to fluorine-containing benzoylguanidines of the formula I

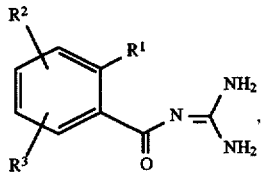

in which $R^1$ is H, F, Cl, Br, I, A, CN, $NO_2$, $C_nF_mH_{2n+1-m}O_p$, alkynyl having 2–4 C atoms or —X—$R^4$, $R^2$ is $C_nF_mH_{2n+1-m}O_p$, $R^3$ is H, A, F, Cl, Br, I, $C_nF_mH_{2n+1m}O_p$, $SO_q$—$R^6$, $SO_2NR^4R^5$, Het, $OR^6$, $SR^6$, S-Het or $NR^7$-Het, $R^4$ and $R^5$ are each independently of one another H or A or else together are alternatively alkylene having 4 to 5 C atoms, where a $CH_2$ group can also be replaced by O, S, NH, NA or

$R^6$ is Ph or A, $R^7$ is H or A,

A is alkyl having 1 to 6 C atoms,

X is O, S or $NR^7$,

Ph is phenyl which is unsubstituted or mono-, di- or trisubstituted by A, OA, $NR^4R^5$, F, Cl, Br, I or $C_nF_mH_{2n+1-m}O_p$, Het is a mono- or binuclear saturated, unsaturated or aromatic heterocyclic radical having 1 to 4 N, O and/or S atoms, which can be unsubstituted or mono-, di- or trisubstituted by F, Cl, Br, $C_nF_mH_{2n+1-m}O_p$, A, X—R , $NO_2$, CN and/or carbonyl oxygen and is bonded to the benzoyl system via N or C, m is 1, 2, 3, 4, 5, 6 or 7, but at most 2n+1, n is 1, 2 or 3, p is 0 or 1 and q is 1 or 2, with the proviso that $R^1$ can only be H if $R^3$ is $SO_q$—$R^6$ or $SO_2NR^4R^5$, and their physiologically acceptable salts.

The invention has an object of finding novel compounds having useful properties, in particular those which can be used for the production of medicaments.

Upon further study of the specification and appended claims, further objects and advantages of this invention will become apparent to those skilled in the art.

It has been found that the compounds of the formula I and their physiologically acceptable salts have useful pharmacological properties together with good tolerability.

The novel compounds are inhibitors of the cellular $Na^+$/$H^+$ antiporter, i.e., active compounds which inhibit the $Na^+$/$H^+$ exchange mechanism of the cells (Düsing et al., Med. Klin. 87, 378–384 (1992)) and which are thus good antiarrhythmics which are suitable, in particular, for the treatment of arrhythmias which occur as a result of oxygen deficiency.

The best known active compound of the acylguanidines group is amiloride. This substance, however, primarily shows a hypertensive and saluretic action, which is undesirable, in particular in the treatment of cardiac arrhythmias, while the antiarrhythmic properties are only very weakly pronounced.

Moreover, structurally similar compounds are known, for example, from EP 0 416 499.

The substances according to the invention of the present application show a good cardioprotective action and are therefore particularly suitable for infarct treatment, infarct prophylaxis and for the treatment of angina pectoris. The substances further act against all pathological hypoxic and ischemic damage, so that the primary or secondary diseases caused thereby can be treated. The active compounds are also highly suitable for preventive applications.

On account of the protective actions of these substances in pathological hypoxia or ischemic situations, further possibilities of application result therefrom in surgical interventions for the protection of temporarily undersupplied organs, in organ transplantations for the protection of the removed organs, in angioplastic vascular or cardiac interventions, in ischaemias of the nervous system, in the therapy of states of shock and for the prevention of essential hypertension.

The compounds can further also be employed as therapeutics in disorders caused by cell proliferation, such as arteriosclerosis, diabetic late complications, cancers, fibrotic disorders, in particular of the lung, liver and kidneys as well as organ hypertrophies and hyperplasias. Moreover, the substances are also suitable for diagnostic use for the recognition of diseases which are accompanied by an increased activity of the $Na^+$/$H^+$ antiporter, e.g. in erythrocytes, platelets or leucocytes.

The actions of the compounds can be determined with the aid of methods known per se, such as are indicated, for example, by N. Escobales and J. Figueroa in J. Membrane Biol. 120, 41–49 (1991) or by L. Counillon, W. Scholz, H. J. Lang and J. Pouysségur in Mol. Pharmacol. 44, 1041–1045 (1993).

Suitable experimental animals are, for example, mice, rats, guinea-pigs, dogs, cats, monkeys or pigs.

The compounds can therefore be used as pharmaceutically active compounds in human and veterinary medicine. They can also be used as intermediates for the preparation of further pharmaceutically active compounds.

In formula I, A is a branched or unbranched alkyl group having 1–6, preferably 1–4, in particular 1, 2 or 3 C atoms, specifically preferably methyl, further preferably ethyl, propyl, isopropyl, butyl, isobutyl, furthermore preferably sec-butyl, tert-butyl, pentyl, isopentyl(3-methylbutyl), hexyl or isohexyl(4-methylpentyl).

$R^1$ is preferably H, particularly preferably A, Cl, Br or else $C_nF_mH_{2n+1-m}O_p$, where $C_nF_mH_{2n+1-m}O_p$ is preferably $CF_3$, $C_2F_5$ or partially fluorinated alkyl having 1–4 C atoms.

$R^2$ is preferably F, Cl, Br or else $C_nF_mH_{2n+1-m}Op$, where $C_nF_mH_{2n+1-m}O_p$ is preferably $OCF_3$, $OCH_2F$, $OCHF_2$, $CF_3$, $C_2F_5$ or partially fluorinated alkyl having 1–4 C atoms, such as $CH_2F$, $CHF_2$, $C_2HF_4$, $C_2H_2F_3$, $C_2H_3F_2$ or $C_2H_4F$.

$R^3$ is preferably $H_3C$—$SO_2$— or $H_2N$—$SO_2$—, but further also preferably hydrogen. One of the two radicals $R^2$ and $R^3$ is preferably in the 4-position, while the other is in the 3- or 5-position of the benzoyl group. An arrangement is particularly preferred, however, in which the radical $R^2$ is in the para-position to the amide group. If the radical $R^3$ is A—$SO_2$—, this is preferably located in the meta-position. A benzoyl group is also particularly preferred which has a methylsulfonyl radical in the 3-position and an alkyl group in the 6-position, preferably methyl or ethyl.

$R^4$ and $R^5$ are preferably H or A.

If $R^4$ and $R^5$ together are alkylene, the alkylene group is preferably unbranched, specifically preferably —$(CH_2)_k$—, where k is 4 or 5; but also preferably —$(CH_2)_2$—O—$(CH_2)_2$—, —$(CH_2)_2$—NH—$(CH_2)_2$—, —$(CH_2)_2$—NA—$(CH_2)_2$—, —$CH_2$—O—$(CH_2)_2$—, —$CH_2$—NH—$(CH_2)_2$— or —CH$_2$—NA—(CH$_2$)$_2$— or —CO—(CH$_2$)$_3$—, —CO—(CH$_2$)$_4$— or —CH$_2$—CO—(CH$_2$)$_2$.

Ph is preferably phenyl which is unsubstituted or monosubstituted by Cl, Br, A, OA, NH$_2$, NHA, NA$_2$ or CF$_3$.

R$^6$ is preferably A, in particular methyl or else preferably also unsubstituted phenyl.

The radical X is preferably O or NH.

Het is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3 or -5-yl, 1,2,3-thiadiazol-4- or -5-yl, 2-, 3-, 4-, 5or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-guinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-quinolinyl, 2-, 4-, 5-, 6-, 7- or 8-quinazolinyl. The heterocyclic radicals can also be partially or completely hydrogenated. Het can thus also be, for example, 2,3-dihydro-2-, -3-, -4- or -5-furyl, 2,5-dihydro-2-, -3-, -4- or -5-furyl, tetrahydro-2- or -3-furyl, - 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or, -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetraydro-1-, -2-, -3-, -4-, -5-, -6-, -7- or -8-quinolinyl, 1,2,3,4-tetrahydro-1-, -2-, -3-, -4-, -5, -6-, -7- or -8-isoquinolinyl.

It applies to the whole invention that all radicals such as Het, Ph or C$_n$F$_m$H$_{2n+1-m}$O$_p$, which occur repeatedly, independently of one another can be identical or different.

Accordingly, the invention relates in particular to those compounds of the formula I in which at least one of the radicals mentioned has one of the preferred meanings indicated above. Some preferred groups of compounds can be expressed by the formulae Ia to Ih below, which correspond to the formula I and in which the radicals which are not designated in greater detail have the meaning indicated in the formula I, but in which in Ia R$^1$ is H and R$^3$ is —SO$_2$—CH$_3$ or —SO$_2$—NH$_2$;

in Ib R$^1$ is H, methyl or ethyl and R$^2$ is CF$_3$, OCF$_3$, OCH$_2$F, OCHF$_2$, C$_2$F$_5$ or partially fluorinated alkyl having 1–4 C atoms, such as CH$_2$F, CHF$_2$, C$_2$HF$_4$, C$_2$H$_2$F$_3$, C$_2$H$_3$F$_2$, C$_2$H$_4$F;

in Ic the radical R$^2$ is C$_n$F$_m$H$_{2n+1-m}$O$_p$ and the radical R$^3$ is hydrogen, CF$_3$, Cl or Br;

in Id R$^1$ is methyl, ethyl, F, Cl or Br and R$^2$ and/or R$^3$ is C$_n$F$_m$H$_{2n+1-m}$O$_p$;

in Ie both radicals R$^2$ and R$^3$ independently of one another are C$_n$F$_m$H$_{2n+1-m}$O$_p$;

in If R$^1$ is methyl, ethyl, F, Cl or Br, R$^2$ is C$_n$F$_m$H$_{2n+1-m}$O$_p$ and R$^3$ is hydrogen;

in Ig the radical C$_n$F$_m$H$_{2n+1-m}$O$_p$, as R$^2$ or R$^3$, is in the p-position to the guanidinocarbonyl group and R$^1$ is methyl, ethyl, F, Cl or Br;

in Ih R$^1$ is NO$_2$ or CN and R$^3$ is C$_n$F$_m$H$_{2n+1-m}$O$_p$.

The invention further relates to a process for the preparation of the compounds of the formula I according to Claim 1, and of their salts, characterized in that a compound of the formula II

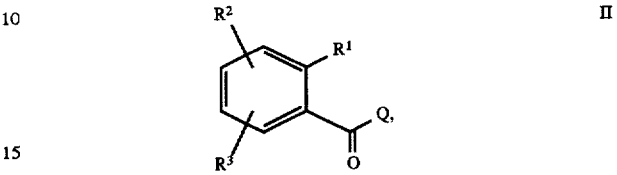

in which R$^1$, R$^2$ and R$^3$ have the meanings indicated above and

Q is Cl, Br, OA, O—CO—A, O—CO—Ph, OH or another reactive esterified OH group or easily nucleophilically substitutable leaving group, is reacted with guanidine, or in that a benzoylguanidine of the formula III

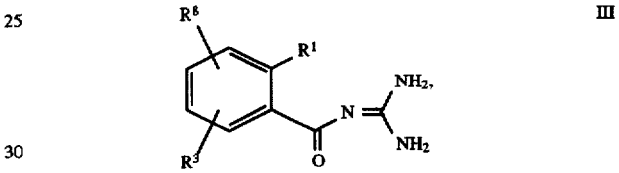

in which R$^1$ and R$^3$ have the meanings indicated above, and R$^8$ is Br, Cl, F, I or another nucleophilically displaceable group, is reacted with a compound of the formula IV

in which n, m and p have the meanings indicated and

L is H, (CH$_3$)$_3$—Si, CO$_2$K or CO$_2$Na, an alkali metal cation, NH$_4^+$, Ag$^+$ or Cu$^+$, or in that a compound otherwise corresponding to the formula I, but which instead of one or more hydrogen atoms contains one or more reducible groups and/or one or more additional C-C and/or C-N bonds, is treated with a reducing agent, or in that a compound otherwise corresponding to the formula I, but which instead of one or more hydrogen atoms contains one or more solvolyzable groups, is treated with a solvolyzing agent and/or in that a base of the formula I which is obtained is converted into one of its salts by treating with an acid.

The compounds of the formula I are otherwise prepared by methods known per se, as are described in the literature (e.g., in the standard works such as Houben-Weyl, Methoden der organischen Chemie (Methods of Organic Chemistry), Georg-Thieme-Verlag, Stuttgart; Organic Reactions, John Wiley & Sons, Inc., New York; and also in the patent application, EP 0 416 499, indicated above), namely under reaction conditions which are known and suitable for the reactions mentioned. In this case, use can also be made of variants which are known per se, but not mentioned here in greater detail.

If desired, the starting substances can also be formed in situ in such a way that they are not isolated from the reaction mixture, but immediately reacted further to give the compounds of the formula I.

Preferably, compounds of the formula I are prepared by reacting an activated carboxylic acid derivative of the formula II, where Q is particularly preferably Cl or —O—CH$_3$, with guanidine. Reaction variants are particularly suitable in which the free carboxylic acid II (Q=OH) is reacted in a manner known per se to give the respective activated derivative and this is then reacted directly with guanidine, without intermediate isolation. Methods in which intermediate isolation is unnecessary are, for example, activation with carbonyldiimidazole, dicyclohexylcarbodiimide or the Mukaiyama variant (Angew. Chem. 91, 788–812 (1979)).

The carboxylic acids of the formula II are prepared by nucleophilic aromatic substitution starting from suitable benzoic acids by reaction with appropriate compounds of the formula IV. The reaction is carried out in analogy to the reaction of the compounds III and IV. It is described below.

Particularly suitable compounds of the formula IV are, for example, alkali metal salts of partially or completely fluorinated alkanecarboxylic acids.

The reaction of a reactive carboxylic acid derivative of the formula II with guanidine is carried out in a manner known per se, preferably in a protic or aprotic polar or non-polar inert organic solvent.

Suitable solvents are mentioned below for the reaction of the compounds III and IV. Particularly preferred solvents, however, are methanol, THF, dimethoxyethane, dioxane or mixtures which can be prepared therefrom as well as water. Suitable reaction temperatures are, for example, temperatures from 20° C. to the boiling point of the solvent. The reaction times are preferably from 5 min. to 12 hours. It is expedient to employ an acid scavenger in the reaction. Those suitable are any types of bases which do not interfere in the reaction. However, the use of inorganic bases such as potassium carbonate or of organic bases such as triethylamine or pyridine or else an excess of guanidine is particularly suitable.

Compounds of the formula I according to claim 1 can further be prepared by reacting a benzoylguanidine of the formula III with a compound of the formula IV. The starting substances of the formula III can be prepared in a simple manner by reaction of appropriately substituted benzoic acids or reactive acid derivatives which can be derived therefrom, such as acid halides, esters or anhydrides, with guanidine under reaction conditions such as are known per se and generally customary for amide preparation. In turn, particularly suitable are those reaction variants such as have been indicated above for the reaction of compound II with guanidine.

Like the methods for their preparation, the compounds of the formula IV are known per se. If they are not known, they can be prepared by the methods known per se.

The preparation of the compound II and the reaction of the compound III with the compound of the formula IV is carried out in a manner known per se, preferably in a protic or aprotic polar inert organic solvent.

In the preparation of II, in the reaction of II with guanidine or in the reaction of III with IV, it is likewise expedient to work in the presence of a base or with an excess of the basic component. Suitable bases are preferably, for example, alkali metal or alkaline earth metal hydroxides, carbonates, alkoxides or organic bases such as triethylamine or pyridine, which are also used in excess and can then simultaneously serve as a solvent.

Suitable inert solvents are, in particular, preferably alcohols such as methanol, ethanol, isopropanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; nitriles such as acetonitrile; nitro compounds such as nitromethane or nitrobenzene; esters such as ethyl acetate; amides such as hexamethylphosphoramide; sulfoxides such as dimethyl sulfoxide (DMSO); chlorinated hydrocarbons such as dichloromethane, chloroform, trichloroethylene, 1,2-dichloroethane or carbon tetrachloride; hydrocarbons such as benzene, toluene or xylene. Mixtures of these solvents with one another are furthermore suitable.

A particularly preferred procedure consists in reacting an excess of a compound IV in the form of the trimethylsilyloxy derivative directly without addition of solvent with a benzoylguanidine of the formula III at temperatures preferably from 100° C. to 400° C., particularly preferably 100° C. to 200° C. A compound of the formula IV, preferably a potassium or a sodium salt or a corresponding carboxylic acid salt, can be reacted in the presence of CuI with the benzoylguanidine of the formula III or a suitable precursor, e.g. an ester.

Furthermore, one or more radicals $R^1$, $R^2$ and/or Het can be converted into other radicals $R^1$, $R^2$ and/or Het in a compound of the formula I.

For example, it is possible to replace an H atom by a halogen atom by means of halogenation or a nitro group by means of nitration and/or to reduce a nitro group to an amino group and/or to alkylate or acylate an amino or hydroxyl group and/or to remove a benzyl radical hydrogenolytically (e.g. with $H_2$ on a catalyst such as Pd or with ammonium formate in methanol).

Nitration is carried out under customary conditions, e.g. using a mixture of concentrated $HNO_3$ and concentrated $H_2SO_4$ at temperatures from 0° C. to 30° C.

The same applies for halogenation, which can be carried out, for example, using elemental chlorine or bromine in one of the customary inert solvents at temperatures from approximately 0° C. to 30° C.

A primary or secondary amino group and/or an OH group can be converted into the corresponding secondary or tertiary amino group and/or alkoxy group by treating with alkylating agents. Suitable alkylating agents are, for example, compounds of the formulae A-Cl, A-Br or A-I or corresponding sulfuric acid or sulfonic acid esters such as methyl chloride, bromide or iodide, dimethyl sulfate or methyl p-toluenesulfonate. It is further possible to introduce, for example, one or two methyl groups using formaldehyde in the presence of formic acid. The alkylation is expediently performed in the presence or absence of one of the inert solvents mentioned, e.g., DMF, at temperatures from approximately 0° C. to approximately 120° C., it also being possible for a catalyst to be present, preferably a base such as potassium tert-butoxide or NaH.

A base of the formula I can be converted into the associated acid addition salt using an acid. For this reaction, suitable acids are those which yield physiologically acceptable salts. Inorganic acids can thus be used, e.g. sulfuric acid, nitric acid, hydrohalic acids such as hydrochloric acid or hydrobromic acid, phosphoric acids such as orthophosphoric acid, sulfamic acid, and further organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids and laurylsulfuric acid.

The compounds of the formula I and their physiologically acceptable salts can be used for the production of pharmaceutical preparations, in particular by a non-chemical route. In this context, they can be brought into a suitable dose form together with at least one solid, liquid and/or semi-liquid excipient or auxiliary and if appropriate in combination with one or more other active compounds.

The invention further relates to compositions, in particular pharmaceutical preparations, comprising at least one compound of the formula I and/or one of its physiologically acceptable salts.

These preparations can be used as medicaments in human or veterinary medicine. Suitable excipients are organic or inorganic substances which are suitable for enteral (e.g. oral) or parenteral administration or topical application and do not react with the novel compounds, for example water, vegetable oils, benzyl alcohols, polyethylene glycols, glycerol triacetate, gelatin, carbohydrates such as lactose or starch, magnesium stearate, talc, lanolin or petroleum jelly. Tablets, coated tablets, capsules, syrups, juices or drops are used, in particular, for oral administration, suppositories for rectal administration, solutions, preferably oily or aqueous solutions, and further suspensions, emulsions or implants, for parenteral administration, ointments, creams, pastes, lotions, gels, sprays, foams, aerosols, solutions (e.g. solutions in alcohols such as ethanol or isopropanol, acetonitrile, DMF, dimethylacetamide, 1,2-propanediol or mixtures thereof with one another and/or with water) or powders for topical application. The novel compounds can also be lyophilized and the lyophilizates obtained used, for example, for the production of injection preparations.

In particular, liposomal preparations are also suitable for topical application. The preparations indicated can be sterilized and/or contain auxiliaries such as lubricants, preservatives, stabilizers and/or wetting agents, emulsifiers, salts for affecting the osmotic pressure, buffer substances, colorants, flavorings and/or aromatic substances. They can, if desired, also contain one or more further active compounds, e.g. one or more vitamins.

The compounds of the formula I and their physiologically acceptable salts can be administered to humans or animals, in particular mammals such as monkeys, dogs, cats, rats or mice and used in the therapeutic treatment of the human or animal body and also in the control of illnesses, in particular in the therapy and/or prophylaxes of disorders of the cardiovascular system. They are therefore suitable for the treatment of arrhythmias, in particular if these are caused by oxygen deficiency, of angina pectoris, infarcts, ischaemias of the nervous system such as, for example, stroke or cerebral oedema, of states of shock and for preventive treatment.

The substances can further be employed as therapeutics in disorders in which cell proliferation plays a part, such as arteriosclerosis, diabetic late complications, cancers, fibroses, and also organ hypertrophies and hyperplasias.

In these contexts, the substances according to the invention are generally administered in analogy to known antiarrhythmics, e.g., aprindine, preferably in doses from approximately 0.01 to 5 mg, in particular from 0.02 to 0.5 mg per dose unit. The daily dose is preferably from approximately 0.0001 to 0.1, in particular from 0.0003 to 0.01, mg/kg, of body weight. The specific dose for each intended patient depends, however, on all sorts of factors, for example on the activity of the specific compound employed, on the age, body weight, the general state of health, the sex, on the diet, on the time and route of administration, and on the excretion rate, pharmaceutical substance combination and severity of the particular disorder to which the therapy applies. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application 195 17 848.3, filed May 16, 1995, are hereby incorporated by reference.

EXAMPLES

In the following examples "customary working up" means: water is added, if necessary, the mixture is extracted with an organic solvent such as ethyl acetate, and the organic phase is separated off, dried over sodium sulfate, filtered, evaporated and purified by chromatography and/or crystallization.

Example 1

A solution of 0.5 g of 2-methyl-4-phenoxy5-trifluoromethylbenzoic acid [obtainable by reaction of methyl 2-methyl-4-phenoxy-5-bromobenzoate with potassium trifluoroacetate in the presence of CuI and tetramethylammonium iodide and subsequent hydrolysis] and 300 mg of carbonyldiimidazole in 15 ml of THF is stirred at room temperature for two hours and then added to 383 mg of guanidine. The mixture is stirred for a further two hours. After customary working up, N-diaminomethylene-2-methyl-4-phenoxy-5-trifluoromethylbenzamide is obtained.

The following are obtained analogously by reaction of guanidine with 2-methyl-5-difluoromethoxybenzoic acid N-diaminomethylene-2-methyl-5-difluoromethoxybenzamide;

with 2-methyl-5-(2,2,2-trifluoroethoxy)benzoic acid N-diaminomethylene-2-methyl-5-(2,2,2-trifluoroethoxy) benzamide;

with 3-methylsulfonyl-4-(pentafluoroethyl)benzoic acid N-diaminomethylene-3-methylsulfonyl-4-(pentafluoroethyl)benzamide;

with 3-methylsulfonyl-4-trifluoromethoxybenzoic acid N-diaminomethylene-3-methylsulfonyl-4-trifluoromethoxybenzamide;

with 3-methylsulfonyl-4-difluoromethoxybenzoic acid N-diaminomethylene-3-methylsulfonyl-4-difluoromethoxybenzamide;

with 3-methylsulfonyl-4-fluoromethoxybenzoic acid N-diaminomethylene-3-methylsulfonyl-4-fluoromethoxybenzamide;

with 2-methyl-4-pentafluoroethyl-5-methylsulfonylbenzoic acid N-diaminomethylene-2-methyl-4-pentafluoroethyl5-methylsulfonylbenzamide;

with 2-methyl-4-trifluoromethoxy-5-methylsulfonylbenzoic acid N-diaminomethylene-2-methyl-4-trifluoromethoxy-5-methylsulfonylbenzamide;

with 2-methyl-4-difluoromethoxy-5-methylsulfonylbenzoic acid N-diaminomethylene-2-methyl-4-difluoromethoxy-5-methylsulfonylbenzamide;

with 2-methyl-4-fluoromethoxy-5-methylsulfonylbenzoic acid N-diaminomethylene-2-methyl-4-fluoromethoxy5-methylsulfonylbenzamide;

with 3-methylsulfonyl-4-(1,6-dihydro-6-oxo-3-pyridazinyloxy)-6-trifluoromethylbenzoic acid N-diaminomethylene-3-methylsulfonyl-4-(1,6-dihydro-6-oxo-3-pyridazinyloxy)-6-trifluoromethylbenzamide.

Example 2

1.1 g of methyl 3-methylsulfonyl-4-trifluoromethylbenzoate [m.p. 146°–147°; obtainable by reaction of methyl 3-methylsulfonyl-4-bromobenzoate with potassium trifluoroacetate in the presence of CuI and tetramethylammonium iodide in toluene] are added to a solution of 928 mg of guanidine in 15 ml of methanol. The mixture is stirred for 45 minutes at 50° and, after removal of the solvent and customary working up, N-diaminomethylene3-methylsulfonyl-4-trifluoromethylbenzamide, m.p. 233°–234°, is obtained.

After treatment with dilute aqueous HCl solution and freeze-drying, the corresponding hydrochloride is obtained therefrom.

The following are obtained analogously by reaction of guanidine with methyl 2-methyl-4-trifluoromethyl-5-methylsulfonylbenzoate (m.p. 135°–136°) N-diaminomethylene-2-methyl-4-trifluoromethyl5-methylsulfonylbenzamide, m.p. 212°–213° (base), hydrochloride;

with methyl 2,5-bis(2,2,2-trifluoroethoxy)benzoate N-diaminomethylene-2,5-bis(2,2,2-trifluoroethoxy) benzamide, hydrochloride;

with methyl 2-methyl-4-bromo-5-trifluoromethoxybenzoate N-diaminomethylene-2-methyl-4-bromo-5-trifluoromethoxybenzamide, hydrochloride;

with methyl 2-ethyl-4-bromo-5-trifluoromethoxybenzoate N-diaminomethylene-2-ethyl-4-bromo-5-trifluoromethoxybenzamide, hydrochloride;

with methyl 2,4-dibromo-5-trifluoromethoxybenzoate N-diaminomethylene-2,4-dibromo-5-trifluoromethoxybenzamide, hydrochloride;

with methyl 2-isopropyl-4-bromo-5-trifluoromethoxybenzoate N-diaminomethylene-2-isopropyl-4-bromo-5-trifluoromethoxybenzamide, hydrochloride;

with methyl 2-isopropyl-4-chloro-5-trifluoromethoxybenzoate N-diaminomethylene-2-isopropyl-4-chloro-5-trifluoromethoxybenzamide, hydrochloride;

with methyl 2-methyl-4-chloro-5-trifluoromethoxybenzoate N-diaminomethylene-2-methyl-4-chloro-5-trifluoromethoxybenzamide, hydrochloride;

with methyl 2-methyl-4-cyano-5-trifluoromethoxybenzoate N-diaminomethylene-2-methyl-4-cyano-5-trifluoromethoxybenzamide, hydrochloride;

with methyl 2-nitro-4-chloro-5-trifluoromethoxybenzoate N-diaminomethylene-2-nitro-4-chloro-5-trifluoromethoxybenzamide, hydrochloride;

with methyl 2-nitro-4-bromo-5-trifluoromethoxybenzoate N-diaminomethylene-2-nitro-4-bromo-5-trifluoromethoxybenzamide, hydrochloride;

with methyl 2,5-bis(trifluoromethoxy)-4-bromobenzoate N-diaminomethylene-2,5-bis(trifluoromethoxy)4-bromobenzamide, hydrochloride;

with methyl 2,5-bis(trifluoromethoxy)-4-chlorobenzoate N-diaminomethylene-2,5-bis(trifluoromethoxy)-5 4-chlorobenzamide, hydrochloride;

with methyl 2,5-bis(trifluoromethoxy)-4-cyanobenzoate N-diaminomethylene-2,5-bis(trifluoromethoxy)4-cyanobenzamide, hydrochloride;

with methyl 2-chloro-5-trifluoromethylbenzoate N-diaminomethylene-2-chloro-5-trifluoromethylbenzamide, hydrochloride, m.p. 205°;

with methyl 2,5-bis(trifluoromethyl)benzoate N-diaminomethylene-2,5-bis(trifluoromethyl)benzamide, hydrochloride, m.p. 232°;

with methyl 2,4-bis(trifluoromethyl)benzoate N-diaminomethylene-2,4-bis(trifluoromethyl)benzamide, hydrochloride, m.p. 179°;

with methyl 2,3-bis(trifluoromethyl)benzoate N-diaminomethylene-2,3-bis(trifluoromethyl)benzamide, hydrochloride;

with methyl 2-methyl-4-bromo-5-trifluoromethylbenzoate N-diaminomethylene-2-methyl-4-bromo-5-trifluoromethylbenzamide, hydrochloride;

with methyl 2-ethyl-4-bromo-5-trifluoromethylbenzoate N-diaminomethylene-2-ethyl-4-bromo-5-trifluoromethylbenzamide, hydrochloride;

with methyl 2,4-dibromo-5-trifluoromethylbenzoate N-diaminomethylene-2,4-dibromo-5-trifluoromethylbenzamide, hydrochloride;

with methyl 2-isopropyl-4-bromo-5-trifluoromethylbenzoate N-diaminomethylene-2-isopropyl-4-bromo-5-trifluoromethylbenzamide, hydrochloride;

with methyl 2-isopropyl-4-chloro-5-trifluoromethylbenzoate N-diaminomethylene-2-isopropyl-4-chloro-5trifluoromethylbenzamide, hydrochloride;

with methyl 2-methyl-4-chloro-5-trifluoromethylbenzoate N-diaminomethylene-2-methyl-4-chloro-5-trifluoromethylbenzamide, hydrochloride;

with methyl 2-methyl-4-cyano-5-trifluoromethylbenzoate N-diaminomethylene-2-methyl-4-cyano-5-trifluoromethylbenzamide, hydrochloride;

with methyl 2-nitro-4-chloro-5-trifluoromethylbenzoate N-diaminomethylene-2-nitro-4-chloro-5-trifluoromethylbenzamide, hydrochloride;

with methyl 2-nitro-4-bromo-5-trifluoromethylbenzoate N-dianinomethylene-2-nitro-4-bromo-5-trifluoromethylbenzamide, hydrochloride;

with methyl 2,5-bis(trifluoromethyl)-4-bromobenzoate N-diaminomethylene-2,5-bis(trifluoromethyl)4-bromobenzamide, hydrochloride;

with methyl 2,5-bis(trifluoromethyl)-4-chlorobenzoate N-diaminomethylene-2,5-bis(trifluoromethyl)-4-chlorobenzamide, hydrochloride;

with methyl 2,5-bis(trifluoromethyl)-4-cyanobenzoate N-diaminomethylene-2 ,5-bis (trifluoromethyl)-4-cyanobenzamide, hydrochloride.

Example 3

The following are obtained analogously to Example 2 by reaction of guanidine with methyl 2-nitro-5-trifluoromethylbenzoate N-diaminomethylene-2-nitro-5-trifluoromethylbenzamide, hydrochloride;

with methyl 2-methyl-5-trifluoromethylbenzoate N-diaminomethylene-2-methyl-5-trifluoromethylbenzamide, hydrochloride;

with methyl 2-ethyl-5-trifluoromethylbenzoate N-diaminomethylene-2-ethyl-5-trifluoromethylbenzamide, hydrochloride;

with methyl 2-butyl-5-trifluoromethylbenzoate N-diaminomethylene-2-butyl-5-trifluoromethylbenzamide, hydrochloride;

with methyl 2-tert-butyl-5-trifluoromethylbenzoate N-diaminomethylene-2-tert-butyl-5-trifluoromethylbenzamide, hydrochloride;

with methyl 2-propyl-5-trifluoromethylbenzoate N-diaminomethylene-2-propyl-5-trifluoromethylbenzamide, hydrochloride;

with methyl 2-isopropyl-5-trifluoromethylbenzoate N-diaminomethylene-2-isopropyl-5-trifluoromethylbenzamide, hydrochloride;

with methyl 2-fluoro-5-trifluoromethylbenzoate N-diaminomethylene-2-fluoro-5-trifluoromethylbenzamide, hydrochloride;

with methyl 2-fluoro-3-trifluoromethylbenzoate N-diaminomethylene-2-fluoro-3-trifluoromethylbenzamide, hydrochloride;

with methyl 2-fluoro-4-trifluoromethylbenzoate N-diaminomethylene-2-fluoro-4-trifluoromethylbenzamide, hydrochloride.

Example 4

The following are obtained analogously to Example 2 by reaction of guanidine with methyl 2-nitro-5-trifluoromethoxybenzoate N-diaminomethylene-2-nitro-5-trifluoromethoxybenzamide, hydrochloride;

with methyl 2-methyl-5-trifluoromethoxybenzoate N-diaminomethylene-2-methyl-5-trifluoromethoxybenzamide, hydrochloride;

with methyl 2-ethyl-5-trifluoromethoxybenzoate N-diaminomethylene-2-ethyl-5-trifluoromethoxybenzamide, hydrochloride;

with methyl 2-butyl-5-trifluoromethoxybenzoate N-diaminomethylene-2-butyl-5-trifluoromethoxybenzamide, hydrochloride;

with methyl 2-tert-butyl-5-trifluoromethoxybenzoate N-diaminomethylene-2-tert-butyl-5-trifluoromethoxybenzamide, hydrochloride;

with methyl 2-propyl-5-trifluoromethoxybenzoate N-diaminomethylene-2-propyl-5-trifluoromethoxybenzamide, hydrochloride;

with methyl 2-isopropyl-5-trifluoromethoxybenzoate N-diaminomethylene-2-isopropyl-5-trifluoromethoxybenzamide, hydrochloride;

with methyl 2-fluoro-5-trifluoromethoxybenzoate N-diaminomethylene-2-fluoro-5-trifluoromethoxybenzamide, hydrochloride;

with methyl 2-fluoro-3-trifluoromethoxybenzoate N-diaminomethylene-2-fluoro-3-trifluoromethoxybenzamide, hydrochloride;

with methyl 2-fluoro-4-trifluoromethoxybenzoate N-diaminomethylene-2-fluoro-4-trifluoromethoxybenzamide, hydrochloride.

Example 5

The following are obtained analogously to Example 2 by reaction of guanidine with methyl 2,4-dimethyl-5-trifluoromethylbenzoate N-diaminomethylene-2,4-dimethyl-5-trifluoromethylbenzamide, hydrochloride;

with methyl 2-methyl-4-isopropyl-5-trifluoromethylbenzoate N-diaminomethylene-2-methyl-4-isopropyl-5-trifluoromethylbenzamide, hydrochloride;

with methyl 2-ethyl-4-methyl-5-trifluoromethylbenzoate N-diaminomethylene-2-ethyl-4-methyl-5-trifluoromethylbenzamide, hydrochloride;

with methyl 2-butyl-4-tert-butyl-5-trifluoromethylbenzoate N-diaminomethylene-2-butyl-4-tert-butyl5-trifluoromethylbenzamide, hydrochloride;

with methyl 2,4-bis(tert-butyl)-5-trifluoromethylbenzoate N-diaminomethylene-2,4-bis (tert-butyl)-5-trifluoromethylbenzamide, hydrochloride;

with methyl 2-propyl-4-ethyl-5-trifluoromethylbenzoate N-diaminomethylene-2-propyl-4-ethyl-5-trifluoromethylbenzamide, hydrochloride;

with methyl 2,4-diisopropyl-5-trifluoromethylbenzoate N-diaminomethylene-2,4-diisopropyl-5-trifluoromethylbenzamide, hydrochloride;

with methyl 2-fluoro-3-trifluoromethyl-4-methylbenzoate N-diaminomethylene-2-fluoro-3-trifluoromethyl-4-methylbenzamide, hydrochloride.

The following examples relate to pharmaceutical preparations:

Example A: Injection vials

A solution of 100 g of an active compound of the formula I and 5 g of disodium hydrogenphosphate is adjusted to pH 6.5 in 3 l of double-distilled water using 2N hydrochloric acid, sterile filtered, filled into injection vials, lyophilized under sterile conditions and aseptically sealed. Each injection vial contains 5 mg of active compound.

Example B: Suppositories

A mixture of 20 g of an active compound of the formula I is fused with 100 g of soya lecithin and 1400 g of cocoa butter, poured into molds and allowed to cool. Each suppository contains 20 mg of active compound.

Example C: Solution

A solution is prepared from 1 g of an active compound of the formula I, 9.38 g of $NaH_2PO_4 \cdot 2\ H_2O$, 28.48 g of $Na_2HPO_4 \cdot 12\ H_2O$ and 0.1 g of benzalkonium chloride in 940 ml of double-distilled water. The solution is adjusted to pH 6.8, made up to 1 l and sterilized by irradiation. This solution can be used, for example, in the form of eye drops.

Example D: Ointment 500 mg of an active compound of the formula I is mixed with 99.5 g of petroleum jelly under aseptic conditions.

Example E: Tablets

A mixture of 1 kg of active compound of the formula I, 4 kg of lactose, 1.2 kg of potato starch, 0.2 kg of talc and 0.1 kg of magnesium stearate is compressed in a customary manner to give tablets such that each tablet contains 10 mg of active compound.

Example F: Coated tablets

Analogously to Example E, tablets are pressed which are then coated in a customary manner with a coating of sucrose, potato starch, talc, tragacanth and colorant.

Example G: Capsules 2 kg of active compound of the formula I are filled in a customary manner into hard gelatin capsules such that each capsule contains 20 mg of the active compound.

Example H: Ampoules

A solution of 1 kg of active compound of the formula I in 60 l of double-distilled water is sterile filtered, filled into ampoules, lyophilized under sterile conditions and aseptically sealed. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A fluorine-containing benzoylguanidine compound of the formula I

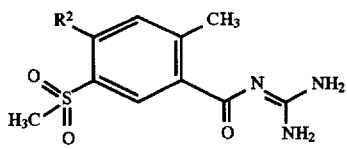

in which
R² is OCF₃ or CF₃ and their physiologically acceptable salts.

2. A compound according to claim 1, which is selected from:
   (a) N-diaminomethylene-2-methyl-4-trifluoromethyl-5-methylsulfonylbenzamide.

3. A process for the production of a pharmaceutical composition comprising bringing a compound of the formula I according to claim 1 and/or one of its physiologically acceptable salts into a suitable dose form together with at least one solid, liquid or semi-liquid excipient or auxiliary.

4. A pharmaceutical composition comprising at least one compound of the formula I according to claim 1 and/or one of its physiologically acceptable salts.

5. A method for treating or preventing an illness indicated by activity of the cellular Na⁺/H⁺ antiporter which comprises administering to a patient a cellular Na⁺/H⁺ antiporter inhibiting effective amount of a compound according to formula I of claim 1 and/or one of its physiologically acceptable salts.

6. A method for treating or preventing an arrhythmia, angina pectoris or an infarct which comprises administering to a patient an effective amount of a compound according to formula I of claim 1 and/or one of its physiologically acceptable salts.

7. The method of claim 5, herein the illness is cardiac arrhythmia, infarct, angina pectoris, an ischaemia of the nervous system, shock, hypertension, arteriosclerosis, diabetic late complications, cancer, a fibrotic disorder or an organ hypertrophy or hyperplasia.

8. A method for inducing a cellular Na⁺/H⁺ antiporter inhibiting effect in a patient which comprises administering to the patient a cellular Na⁺/H⁺ antiporter inhibiting effective amount of a compound according to formula I of claim 1 and/or one of its physiologically acceptable salts.

* * * * *